United States Patent [19]

Schickaneder et al.

[11] Patent Number: 4,599,346
[45] Date of Patent: Jul. 8, 1986

[54] PROPAN-2-OL DERIVATIVES, A PROCESS FOR THEIR PRODUCTION AND MEDICAMENTS CONTAINING THESE COMPOUNDS

[75] Inventors: Helmut Schickaneder, Eckental; Stefan Postius, Nuremberg; Rolf Herter, Schwabach; Peter Mörsdorf, Cadolzburg; Istvan Szelenyi, Schwaig; Kurt H. Ahrens, Nuremberg, all of Fed. Rep. of Germany

[73] Assignee: Ludwig Heumann & Co., GmbH, Nuremberg, Fed. Rep. of Germany

[21] Appl. No.: 630,963

[22] Filed: Jul. 16, 1984

[30] Foreign Application Priority Data

Jul. 22, 1983 [DE] Fed. Rep. of Germany ....... 3326545

[51] Int. Cl.$^4$ .................. A61K 31/41; A61K 31/445; C07D 211/06; C07D 417/12
[52] U.S. Cl. .................................... 514/317; 514/342; 546/209; 546/232
[58] Field of Search ................ 546/209, 232; 514/317, 514/342

[56] References Cited

U.S. PATENT DOCUMENTS 4,374,248  2/1983  Crenshaw et al. .................. 546/209

FOREIGN PATENT DOCUMENTS 0099122  1/1984  European Pat. Off. ............ 546/209
105702   4/1984  European Pat. Off. ............ 546/232

OTHER PUBLICATIONS

Drugs of the Future, vol. 10, No. 1, pp. 51-69, 1985.

*Primary Examiner*—Robert T. Bond
*Attorney, Agent, or Firm*—Walter H. Schneider

[57] ABSTRACT

The invention relates to new propan-2-ol derivatives corresponding to the following general formula

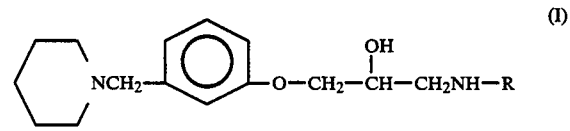

in which R represents

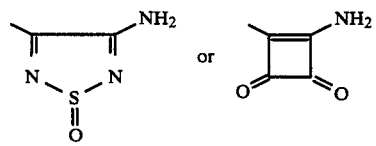

and to salts thereof with pharmacologically acceptable acids. These compounds have a selective effect on histamine-$H_2$-receptors.

2 Claims, No Drawings

PROPAN-2-OL DERIVATIVES, A PROCESS FOR THEIR PRODUCTION AND MEDICAMENTS CONTAINING THESE COMPOUNDS

This invention relates to new propan-2-ol derivatives which have a strong selective effect on histamine-H$_2$-receptors, to a process for their production and to medicaments containing these compounds and, finally, to the use of these compounds for therapeutic purposes.

Cimetidine (Tagamet ®) has already been used in the treatment of ulcers. Unfortunately, cimetidine has a relatively short half life. Because of this, tablets containing doses of 200 to 300 mg in a therapeutically established form have to be administered several times a day. Accordingly, there is a need for anti-ulcer agents which are more active and/or remain active for a longer period than cimetidine.

By virtue of their specific H$_2$-antagonistic activity, the compounds obtainable in accordance with the invention inhibit the secretion of gastric acid when it is stimulated by histamine agonists [Ash and Schild, "Brit. J. Pharmacol. Chemother.", 27, 427 (1966) and Black et al., "Nature", 236, 385 (1971)]. The pharmacological activity of these compounds, which will be described in more detail hereinafter, may be demonstrated by a modified method according to DE-OS No. 27 34 070 in perfused rats' stomachs. In addition, the H$_2$-antagonistic effect can be demonstrated on female Heidenhain-Pouch dogs using the method of Black et al., "Nature", 236, 385 (1971). In addition, the new compounds antagonize the effect of histamine on the frequency of contraction of the isolated right atrium of guinea pigs, but have no effect on histamine-induced contractions of the isolated, smooth gastrointestinal muscle where they are produced by H$_2$-agonists. Since inhibitors for histamine-H$_2$-receptors have an inhibiting effect both in regard to basal gastric acid secretion and also in regard to the secretion of gastric acid induced by gastrin, histamine, methacholine or food, they may be used in the treatment of peptic ulcers caused by the excessive secretion of gastric acid and also in the treatment of hyperacidic gastritis.

The object of the present invention is to provide new inhibitors for histamine-H$_2$-receptors which have an improved and/or longer lasting effect.

This object is achieved by the invention.

The present invention relates to new propan-2-ol derivatives corresponding to the following general formula

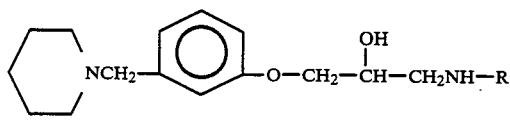

in which R represents

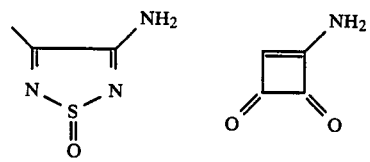

and to salts thereof with pharmacologically acceptable acids.

The salts are formed with suitable acids. Examples ar the hydrochlorides, hydrobromides, sulfates, methane sulfonates, acetates, maleates, succinates, citrates, tartrates, fumarates, benzoates, embonates, etc. and hydrates thereof.

The invention also covers all tautomeric forms and all optically active isomers and salts thereof. The compounds according to the invention corresponding to formula (I) can form disalts which also fall within the scope of the invention.

The compounds according to the invention are produced by a process which is characterized in that a compound corresponding to the following formula

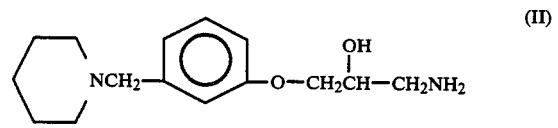

is reacted in known manner (a) with a thiazole derivative corresponding to the following formula

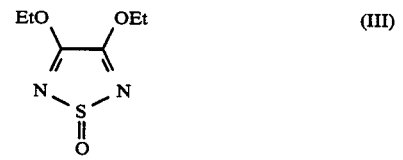

or (b) with a cyclobutane dione derivative corresponding to the following formula

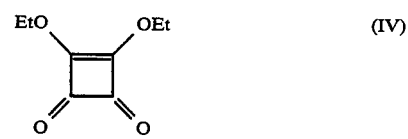

and the compound obtained is reacted with an alcoholic, preferably ethanolic, ammonia solution to form the compounds of general formula (I) according to the invention.

The reaction is carried out at a temperature from room temperature to the boiling temperature of the particular solvent and preferably at 25° C. Suitable solvents are, for example, alcohols, such as methanol, ethanol or isopropanol, preferably ethanol, or ethers, such as dioxane or tetrahydrofuran.

The compound of general formula I obtained is separated off by standard methods, for example by chromatography or crystallization.

The compound of general formula I obtained may be converted into its salts in known manner using a pharmacologically acceptable acid.

The compounds according to the invention, preferably in the form of a salt, may be formulated in any way for administration. Accordingly, the invention also relates to medicaments containing at least one compound according to the invention for use in human or veterinary medicine. The medicaments according to the invention may be conventionally produced using one or more pharmaceutically compatible carriers or diluents.

Accordingly, the compounds according to the invention may be formulated for oral, buccal, topical, parenteral or rectal administration, oral administration being preferred. For oral administration, the medicament may be present, for example, in the form of tablets, capsules, powders, solutions, syrups or suspensions which have been conventionally produced using acceptable diluents. For buccal administration, the medicament may assume the form of tablets or capsules which have been conventionally formulated.

The compounds according to the invention may be formulated for parenteral administration by bolus injection or continuous infusion. Formulations for injection may be present in unit dose form as ampoules or in multiple-dose containers with added preservative.

The medicaments may assume such forms as suspensions, solutions or emulsions in oily or aqueous vehicles and may contain formulation aids, such as suspending agents, stabilizers and/or dispersants. Alternatively, the active principle may even be present in powder form for reconstitution before use with a suitable vehicle, for example sterile, pyrogen-free water.

The compounds according to the invention may also be formulated for rectal preparations, for example suppositories or retention enemas containing, for example, conventional suppository bases, such as cocoa butter or other glycerides.

For topical application, the compounds according to the invention may be conventionally formulated as ointments, creams, gels, lotions, powders or sprays.

For oral administration, a suitable daily dose of compounds according to the invention is from 1 to 4 doses containing a total of up to 5 mg to 1 g per day and preferably 5 to 250 mg per day, depending upon the condition of the patient. In individual cases, it may be necessary to vary the dosage in dependence upon the reaction of the individual to the active principle or its formulation and upon the time at which or intervals at which it is administered. For example, there are cases where it will be sufficient to administer less than the minimum dose specified above, whereas in other cases the dose administered will have to exceed the upper limit indicated.

The compounds according to the invention are distinguished from recognized medicaments acting in the same direction by an improvement in the pharmacological activity levels. This is apparent from the results of the comparative pharmacological studies reported hereinafter.

A recognized method of measuring $H_2$-antagonistic activity is based on determination of the $pA_2$-values in vitro on the isolated atrium of guinea pigs

| | $pA_2$-values | |
| --- | --- | --- |
| Cimetidine | 6.31 | comparison |
| Ranitidine | 6.81 | comparison |
| Example 1 | 7.31 | |
| Example 2 | 7.14 | |

The invention is illustrated by the following Examples.

EXAMPLE 1

4-amino-3-[2-hydroxy-3-[3-(1-piperidinylmethyl)-phenoxy]propyl]-amino-1,2,5-thiadiazole-1-oxide

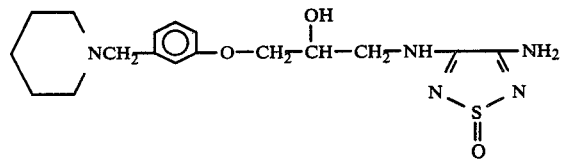

1.33 g (7 mMoles) of 3,4-diethoxy-1,2,5-thiadiazole-1-oxide are added to 1.97 g (7 mMoles) of 1-amino-3-[3-(1-piperidinylmethyl)-phenoxy]-2-propanol dissolved in 50 ml of ethanol, followed by stirring for 18 h at 25° C. 15 ml of a 5N ethanolic ammonia solution are then added, followed by stirring for another 18 h at 25° C. The reaction solution is concentrated in vacuo and the residue purified by column chromatography (silica gel/methanol).

Colorless crystals melting at 144°–146° C.

Yield: 850 mg (33% of the theoretical).

$Rf = 0.57$ (methanol/$NH_3$/$H_2O$ 99:1).

$C_{17}H_{25}N_5O_3S$ (379.5); Calculated: C 53.81, H 6.64; N 18.46, S 8.45. Observed: C 54.22, H 6.82, N 18.08, S 8.66.

$^1H$-NMR-spectrum: ($d_6$-DMSO, TMS as internal standard) $\delta = 1.23$–1.70 (m) (—($CH_2$)$_3$—) 6H, 2.17–2.47 (m) ($CH_2$)$_2$) 4H, 3.39 (s) (N—$CH_2$) 2H, 3.49–3.67 (m) (—$CH_2$—) 2H, 3.83–4.23 (—CH, O—$CH_2$) 3H, 5.44 (m) (exchangeable for $D_2O$) 1H, 6.70–7.4 (m) (aromatic-H) 4H, 8.0 (s, broad) (exchangeable for $D_2O$) 2H, 8.25 (broad) (exchangeable for $D_2O$) 1H ppm.

Preparation of the intermediate stages (a) 2-(oxiranylmethyl)-1H-isoindole-1,3-(2H)-dione

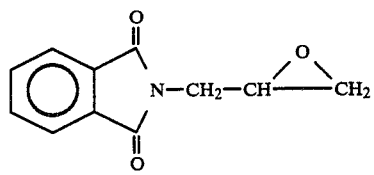

41.1 g (0.3 mole) of epibromohydrin are added to a suspension of 55.6 g (0.3 mole) of potassium phthalimide in 250 ml of dimethyl formamide, followed by heating for 8 h to 100° C. After the reaction solution has cooled, it is poured onto 300 ml of water, followed by extraction with acetic acid ethyl ester. The solvent is then concentrated in vacuo and the residue recrystallized from ethanol/acetic acid ethyl ester/petroleum ether. Colorless crystals melting at 90°–95° C.

Yield: 18.7 g (30.7% of the theoretical).
Rf=0.4 (Al$_2$O$_3$; CH$_2$Cl$_2$).

(b)
2-[2-hydroxy-3-[3-(1-piperidinylmethyl)-phenoxy]-propyl]-1H-isoindole-1,3-(2H)-dione

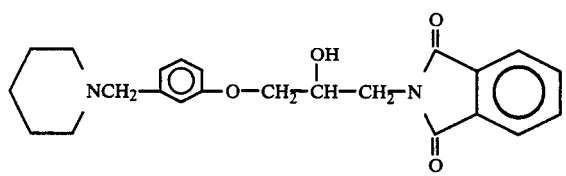

18.7 g (0.092 mole) of 2-(oxiranylmethyl)-1H-isoindole-1,3-(2H)-dione are mixed with 17.5 g (0.092 mole) of 3-(1-piperidinylmethyl)-phenol and the resulting mixture heated for 10 minutes to 130° C. After cooling, the reaction mixture is dissolved in 200 ml of chloroform and the organic phase is washed three times in succession with 30 ml of 1N NaOH-solution, then with 30 ml of water and finally with 30 ml of saturated aqueous NaCl-solution. After the organic phase has been dried over Na$_2$SO$_4$, it is concentrated in vacuo. The residue contains the title compound in the form of a viscous oil.

Yield: 20.1 g (55% of the theoretical)

(c)
1-amino-3-[3-(1-piperidinylmethyl)-phenoxy]-2-propanol

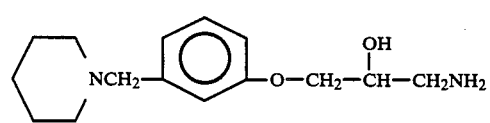

A solution of 7.7 g (0.019 mole) of 2-[2-hydroxy-3-[3-(1-piperidinylmethyl)-phenoxy]-propyl]-1H-isoindole-1,3-(2H)-dione and 2.9 ml of hydrazine hydrate (80% aqueous solution) in 80 ml of ethanol is heated for 3 h to reflux temperature. After the reaction solution has cooled, the solid formed is separated off, the solution is concentrated in vacuo and the residue is dissolved in 80 ml of water. 7.2 ml of conc. HCl are added to the aqueous solution which is then filtered off under suction from the solid precipitated, after which the aqueous solution is adjusted to pH 12 with 2N NaOH and repeatedly extracted with acetic acid ethyl ester. The organic solvent is concentrated in vacuo and the residue purified by distillation (B.p.$_{0.008}$=140°–160° C.). After the addition of petroleum ether to the distillate, the title compound crystallizes out.

Colorless crystals melting at 72°–74° C.
Yield: 1.97 g (39% of the theoretical).

EXAMPLE 2

2-amino-1-[2-hydroxy-3-[3-(1-piperidinylmethyl)-phenoxy]propyl]-aminocyclobut-1-ene-3,4-dione

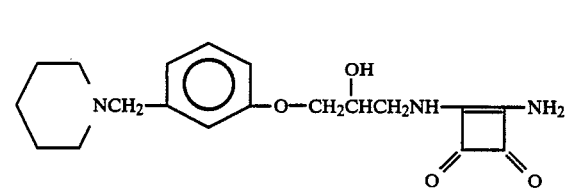

This compound is produced as in Example 1 from 5.28 g (20 mMoles) of 1-amino-3-[3-(1-piperidinylmethyl)-phenoxy]-2-propanol and 3.4 g (20 mMoles) of 1,2-diethoxycyclobut-1-ene-3,4-dione.

Colorless crystals melting at 207°–208° C. (decomp.).
Yield: 3.37 g (47% of the theoretical).
Rf=0.18 (CH$_2$Cl$_2$/MeOH 8:2).
C$_{19}$H$_{25}$N$_3$O$_4$ (359.4): Calculated: C 63.49, H 7.01, N 11.69. Observed: C 63.44, H 7.06, N 11.68.

$^1$H-NMR-spectrum: (d$_6$-DMSO, TMS as internal standard) δ=1.20–1.67 (m) (—(CH$_2$)$_3$) 6H, 2.17–2.47 (m) ((CH$_2$)$_2$) 4H, 3.40 (s) (N—CH$_2$) 2H, 3.50–4.13 (m) (—CH$_2$—, CH,O—CH$_2$, OH) 6H, 6.73–7.40 (m) (aromatic-H) 4H, 7.50 (broad) 3H (exchangeable for D$_2$O) ppm.

We claim:
1. A Propan-2-ol corresponding to the formula:

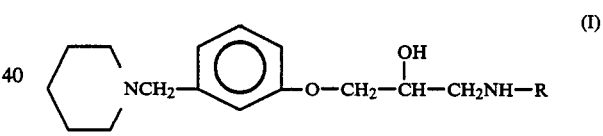

(I)

in which R represents

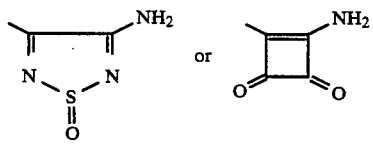

and salts thereof with pharmacologically acceptable acids.

2. A pharmaceutical composition for use in inhibiting the secretion of gastric acid and for the treatment of peptic ulcers and hyperacidic gastritis comprising as the principal active ingredient an effective amount of a propan-2-ol according to claim 1 in admixture with a pharamceutically acceptable carrier.

* * * * *